United States Patent
Kuo et al.

(10) Patent No.: US 11,033,360 B2
(45) Date of Patent: Jun. 15, 2021

(54) PRIORITIZATION OF THREE DIMENSIONAL DENTAL ELEMENTS

(71) Applicant: Align Technology, Inc., San Jose, CA (US)

(72) Inventors: Eric E. Kuo, San Jose, CA (US); Igor Kvasov, Dolgoprudny (RU); Anna Egorova, Protvino (RU); Sergey Gagarin, Lobnya Town (RU)

(73) Assignee: Align Technology, Inc., San Jose, CA (US)

( * ) Notice: Subject to any disclaimer, the term of this patent is extended or adjusted under 35 U.S.C. 154(b) by 745 days.

(21) Appl. No.: 15/824,621

(22) Filed: Nov. 28, 2017

(65) Prior Publication Data

US 2018/0089391 A1 Mar. 29, 2018

Related U.S. Application Data

(63) Continuation of application No. 14/716,537, filed on May 19, 2015, now abandoned, which is a continuation of application No. 13/410,196, filed on Mar. 1, 2012, now Pat. No. 9,037,439.

(60) Provisional application No. 61/486,138, filed on May 13, 2011.

(51) Int. Cl.
| | |
|---|---|
| *A61C 7/00* | (2006.01) |
| *A61C 9/00* | (2006.01) |
| *G06F 30/00* | (2020.01) |
| *G16H 50/50* | (2018.01) |

(Continued)

(52) U.S. Cl.
CPC .......... *A61C 7/002* (2013.01); *A61B 1/00009* (2013.01); *A61B 1/00022* (2013.01); *A61B 1/24* (2013.01); *A61C 9/004* (2013.01); *A61C 9/0053* (2013.01); *A61C 9/0073* (2013.01);

(Continued)

(58) Field of Classification Search
CPC ................................ A61C 9/004; A61C 7/002
See application file for complete search history.

(56) References Cited

U.S. PATENT DOCUMENTS

| | | |
|---|---|---|
| 4,941,164 A | 7/1990 | Schuller et al. |
| 5,775,900 A | 7/1998 | Ginsburg et al. |

(Continued)

OTHER PUBLICATIONS

Anatomage; 3D cephalometric analysis: complete 3D cephalometry tracing and analysis module: 3 pages, as available Jul. 27, 2013: retrieved from the internet (https://web.archive.org/web/20130727190607/http://www.anatomage.com/Product-3DcephAnalysis.html); on Mar. 12, 2020.

(Continued)

*Primary Examiner* — Akash Saxena
(74) *Attorney, Agent, or Firm* — Shay Glenn LLP (57) ABSTRACT

The present disclosure includes methods, systems, and devices for prioritization of three dimensional dental elements. One method for prioritizing three dimensional dental elements includes receiving a virtual initial dental data set (IDDS) of teeth having spatial information regarding the positions of a number of teeth in the virtual IDDS with respect to each other for presentation of the teeth in a virtual three dimensional space to be viewed on a user interface, setting prioritization values of a number of elements of one or more of the number of teeth, and prioritizing the number of elements to be selected by a user based upon their prioritization values.

20 Claims, 5 Drawing Sheets

(51) Int. Cl.
*A61B 1/00* (2006.01)
*A61B 1/24* (2006.01)

(52) U.S. Cl.
CPC ............. *G06F 30/00* (2020.01); *G16H 50/50* (2018.01); *G06T 2210/62* (2013.01)

(56) References Cited

U.S. PATENT DOCUMENTS

| | | | |
|---|---|---|---|
| 6,068,482 A * | 5/2000 | Snow | A61C 7/00 433/223 |
| 6,151,030 A * | 11/2000 | DeLeeuw | G09G 5/02 345/592 |
| 6,227,850 B1 | 5/2001 | Chishti et al. | |
| 6,334,853 B1 * | 1/2002 | Kopelman | A61C 19/05 433/214 |
| 6,371,761 B1 | 4/2002 | Cheang et al. | |
| 6,386,878 B1 * | 5/2002 | Pavlovskaia | A61C 9/0046 433/215 |
| 6,845,175 B2 | 1/2005 | Kopelman et al. | |
| 7,010,150 B1 * | 3/2006 | Pfeiffer | A61C 9/0053 382/128 |
| 7,040,896 B2 | 5/2006 | Pavlovskaia et al. | |
| 7,068,825 B2 | 6/2006 | Rubbert et al. | |
| 7,080,979 B2 | 7/2006 | Rubbert et al. | |
| 7,123,767 B2 | 10/2006 | Jones et al. | |
| 7,156,655 B2 * | 1/2007 | Sachdeva | A61C 7/00 433/24 |
| 7,156,661 B2 * | 1/2007 | Choi | A61C 7/00 433/213 |
| 7,329,122 B1 | 2/2008 | Scott | |
| 7,476,100 B2 | 1/2009 | Kuo | |
| 7,740,476 B2 | 6/2010 | Rubbert et al. | |
| 7,826,646 B2 * | 11/2010 | Pavlovskaia | A61C 7/002 382/128 |
| 7,840,373 B2 | 11/2010 | Culp et al. | |
| 7,942,672 B2 | 5/2011 | Jones et al. | |
| 7,987,099 B2 | 7/2011 | Kuo et al. | |
| 8,099,268 B2 | 1/2012 | Kitching et al. | |
| 8,170,327 B2 | 5/2012 | Glor et al. | |
| 8,194,067 B2 | 6/2012 | Raby et al. | |
| 8,275,180 B2 | 9/2012 | Kuo | |
| 8,465,280 B2 | 6/2013 | Sachdeva et al. | |
| 9,037,439 B2 * | 5/2015 | Kuo | A61B 1/24 703/1 |
| 9,211,166 B2 | 12/2015 | Kuo et al. | |
| 2001/0038705 A1 | 11/2001 | Rubbert et al. | |
| 2002/0010568 A1 | 1/2002 | Rubbert et al. | |
| 2002/0015934 A1 | 2/2002 | Rubbert et al. | |
| 2002/0039717 A1 * | 4/2002 | Amber | A61C 8/0001 433/172 |
| 2002/0055081 A1 | 5/2002 | Hughes et al. | |
| 2002/0177108 A1 * | 11/2002 | Pavlovskaia | A61C 5/77 433/215 |
| 2002/0180760 A1 | 12/2002 | Rubbert et al. | |
| 2003/0008259 A1 * | 1/2003 | Kuo | A61C 7/08 433/6 |
| 2003/0096210 A1 | 5/2003 | Rubbert et al. | |
| 2003/0169913 A1 | 9/2003 | Kopelman et al. | |
| 2004/0029068 A1 | 2/2004 | Sachdeva et al. | |
| 2004/0038168 A1 * | 2/2004 | Choi | A61C 7/00 433/24 |
| 2004/0197727 A1 * | 10/2004 | Sachdeva | A61C 13/0004 433/24 |
| 2005/0048432 A1 * | 3/2005 | Choi | A61C 7/00 433/24 |
| 2005/0192835 A1 | 9/2005 | Kuo et al. | |
| 2006/0093206 A1 * | 5/2006 | Rubbert | A61C 9/006 382/154 |
| 2006/0263738 A1 | 11/2006 | Kuo | |
| 2008/0300824 A1 | 12/2008 | Culp et al. | |
| 2009/0034811 A1 | 2/2009 | Kuo | |
| 2009/0098502 A1 * | 4/2009 | Andreiko | G16H 50/50 433/24 |
| 2009/0133260 A1 | 5/2009 | Durbin et al. | |
| 2009/0148809 A1 | 6/2009 | Kuo et al. | |
| 2009/0291417 A1 | 11/2009 | Rubbert | |
| 2011/0102549 A1 * | 5/2011 | Takahashi | A61C 1/084 348/46 |
| 2011/0224955 A1 * | 9/2011 | Fisker | B33Y 80/00 703/1 |
| 2011/0270588 A1 | 11/2011 | Kuo et al. | |
| 2012/0072178 A1 * | 3/2012 | Beaudry | A61C 13/0004 703/1 |
| 2012/0282572 A1 * | 11/2012 | MacLeod | A61C 9/004 433/202.1 |
| 2012/0287130 A1 | 11/2012 | Rhee et al. | |
| 2012/0290269 A1 * | 11/2012 | Kuo | G16H 50/50 703/1 |
| 2014/0313304 A1 * | 10/2014 | Adriaens | A61C 11/005 348/77 |
| 2015/0254420 A1 * | 9/2015 | Kuo | G06F 30/00 703/11 |
| 2018/0089391 A1 * | 3/2018 | Kuo | A61B 1/00009 |
| 2020/0205948 A1 * | 7/2020 | Prestipino | A61C 8/0048 |

OTHER PUBLICATIONS

Anatomage; Invivo5: anatomy imaging software; 3 pages, as available Jul. 27, 2013; retrieved from the internet (https://web.archive.org/web/20130727034839/http://www.anatomage.com/Product-Invivodental.html); on Mar. 12, 2020.

Anatomage; Medical Design Studio; 5 pages, as available Aug. 10, 2013; retrieved from the internet (https://web.archive.org/web/20130810034114/http://www.anatomage.com/Product-MedicalDesignStudio.html); on Mar. 12, 2020.

Anatomage; Stitching: double your 3D field of view, double the value of your CBCT machine!; 1 page, as available Jan. 15, 2013; retrieved from the interent (https://web.archive.org/web/20130115045607/http://anatomage.com/Product-OptionalModules.html): on Mar. 12, 2020.

Anatomage; The most advanced digital solution to CBCT users; 2 pages, as available May 27, 2013; retrieved from the internet (https://web.archive.org/web/20130527195408/http://www.anatomage.com/Product-Anatomodel.html) on Mar. 12, 2020.

Anatomage; Visage: interactive 3D touch workstation; 3 pages, as available Jan. 15, 2013; retrieved from the internet (https://web.archive.org/web/20130115045456/http://www.anatomage.com/Product-Visage.html); on Mar. 12, 2020.

* cited by examiner

PRIORITIZATION OF THREE DIMENSIONAL DENTAL ELEMENTS

PRIORITY INFORMATION

This application is a Continuation of U.S. application Ser. No. 14/716,537, filed May 19, 2015, which is a Continuation of U.S. application Ser. No. 13/410,196, now U.S. Pat. No. 9,037,439, filed Mar. 1, 2012, which claims the benefit of U.S. Provisional Application No. 61/486,138, the specification of which is incorporated herein by reference.

TECHNICAL FIELD

The present disclosure relates to methods, systems, and devices for prioritization of three dimensional dental elements.

BACKGROUND

The ability to visualize and manipulate key digital dental references in a three dimensional (3D) scene can be important for efficiency, making 3D computerized graphics more efficient, at times, than physical manipulation of models. However, digital dental references may be incorrectly identified in these 3D computerized graphics as a result of certain surfaces (e.g., interproximal surfaces) being blocked out due to crowding. Furthermore, identifying a correct surface may be difficult when teeth are worn down, broken, or restored to an atypical shape.

DETAILED DESCRIPTION

Embodiments of the present disclosure include methods, systems, and devices for prioritization of three dimensional (3D) dental elements. For example, one or more embodiments include a method of prioritizing 3D dental elements that includes receiving a virtual initial dental data set (IDDS) of teeth having spatial information regarding the positions of a number of teeth in the virtual IDDS with respect to each other for presentation of the teeth in a virtual 3D space to be viewed on a user interface, setting prioritization values of a number of elements of one or more of the number of teeth, and prioritizing the number of elements to be selected by a user based upon their prioritization values.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that process, electrical, or mechanical changes may be made without departing from the scope of the present disclosure.

Embodiments of the present disclosure can be utilized, for example, to solve the problem of landmarks being incorrectly identified as a result of certain surfaces, such as interproximal surfaces, being blocked out due to crowding. Embodiments also can solve the problem of trying to identify the correct surface when teeth are worn down, broken, or restored to an atypical shape, making the identification difficult to perform accurately. By using the context in which the tooth is positioned, the landmark can be properly labeled with one or more desired landmark labels despite the non-conventional position and/or shape of the tooth or tooth-related surface.

The process of labeling the digital landmarks therefore depends on the user's ability to visualize the surrounding dental-related geometries, as well as the relevant landmarks, and the ability to position the landmarks in the proper position in 3D space. This may entail the desire to see through objects and access a reference point behind the object, and/or for the object to be adhered to a certain surface contour.

A 3D object, when viewed, may have a natural spatial sequence of prioritization, meaning that the surface closest to the viewer has first priority, and the surface farthest away from the viewer has the least. It may be desirable for 3D manipulation purposes to orient the object in a certain view, but disrupt the natural sequence of prioritization. In other words, it may be desirable to be able to select the second closest surface first instead of the first closest object.

For example, in a number of embodiments, a user can specify which "layer" of an object (e.g., a tooth) should always take priority. By doing this, the user can create automation commands, for example, whereby keystrokes on the keyboard will advance to the next priority independent of the view.

Furthermore, in a number of embodiments, a user can choose to have relative priority, meaning that rather than having to specify which object (e.g., a tooth) has priority over the other, there may be general classifications, whereby a type of element has priority over another family of elements. For instance, in a number of embodiments, teeth surfaces may always have priority over gingival (gum) surfaces. In such embodiments, it may be that a user will always be able to select the teeth before the gums, but can advance to the gums by selecting a keystroke, for example.

In some embodiments, a priority as to which objects are to be rendered transparent and which to be left opaque can be given depending on which object is selected. This allows for user input or an automatic (determined via computing device executable instructions) determination as to which object is made more transparent and which object is more opaque (e.g., solid).

Figure 1:
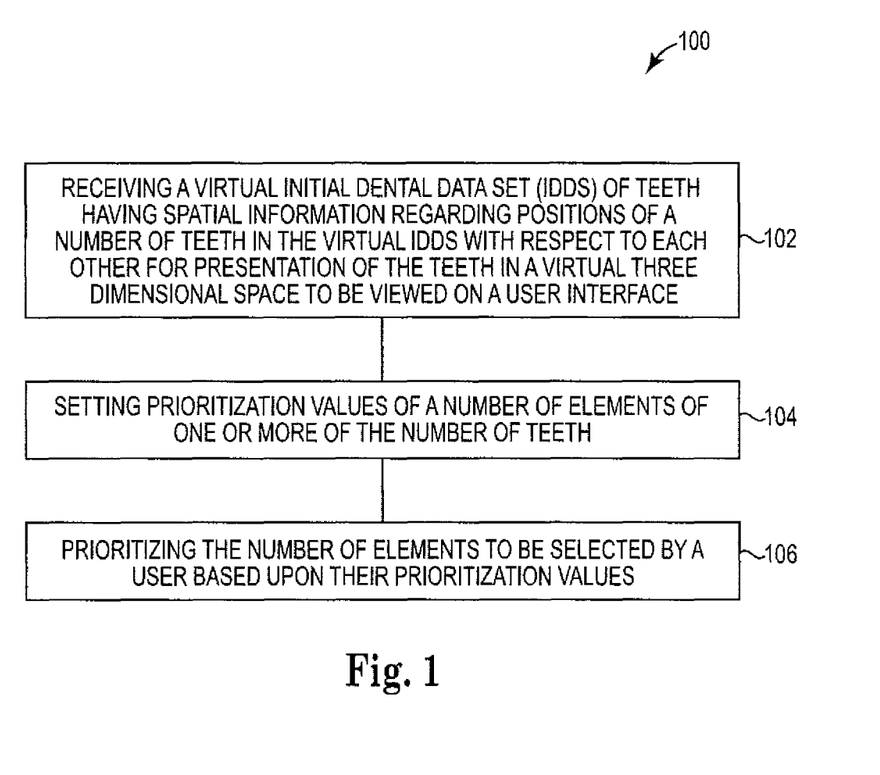
FIG. 1 illustrates a method for prioritizing three-dimensional (3D) dental elements according to one or more embodiments of the present disclosure.

FIG. 1 illustrates a method 100 for prioritizing 3D dental elements according to one or more embodiments of the present disclosure. At 102, a virtual IDDS of teeth having spatial information regarding the positions of multiple teeth in the virtual IDDS with respect to each other for presentation of the teeth in a virtual three dimensional space to be viewed on a user interface is received.

An IDDS and/or virtual IDDS representing an initial tooth arrangement may be obtained in a variety of ways. For example, a patient's teeth may be imaged to obtain digital data using direct or indirect structured light, X-rays, three-dimensional X-rays, computer-aided tomographic images or data sets, magnetic resonance images, photographic reconstruction, and/or other imaging techniques.

Prioritization values of a number of elements of one or more of the number of teeth are set at 104. In some embodiments, prioritization values can be set by a user, such as a dental service provider, and in other embodiments, prioritization values can be determined by instructions executed by a processor. Prioritization values can also be set, for example, based on elements, landmarks, or dental objects in a virtual IDDS.

Elements can include, among others, a tooth and/or teeth in the virtual IDDS, a reference point on and/or around a tooth and/or teeth in the virtual IDDS, a dental object, and/or a dental landmark, such as, for example a crown, a root, a surface, a cusp, a cingulum, a ridge, a developmental groove, etc. Elements can also include, for instance, a combination of the previously discussed elements. In some embodiments, an element is attached to a tooth and/or teeth in the virtual IDDS.

At 106, elements to be selected by a user are prioritized based upon their prioritization values. In some embodiments, using the prioritization values, a first element in the number of elements can be allowed to be selected before a second element in the number of elements, where the first and second elements may have overlapping portions. The first and second elements may also be located on a same tooth or on different teeth. Based on the selection, in some embodiments, one of the first element and the second element can be rendered more (e.g., automatically rendered) transparent, while the other element is rendered more opaque.

Elements can also be manipulated along a tooth and/or teeth in a virtual IDDS, and this can influence decisions about an element's transparency. For instance, in some embodiments, such as for manipulating objects attached to a tooth where the relevant surface is facing the user, the tooth can be more opaque, but a neighboring tooth can be made more transparent.

In such embodiments, the tooth may not be made invisible because the adjacent tooth can be a beneficial reference in the positioning of the reference point on the more opaque tooth. A line of sight of a user can also be considered, and a particular element in the virtual IDDS can be automatically rendered more transparent based on the line of sight consideration. In some embodiments, digital dental landmarks can also be identified on a tooth and/or teeth in the virtual IDDS despite unconventional and/or inconvenient positions of the landmark.

The identified digital dental landmark can also be transferred to a different virtual dental data set in a number of embodiments. For example, a landmark may be adjusted on a first model (e.g., a virtual IDDS) to be propagated across different time points of the same model for a same patient. In such embodiments, the different virtual dental data set may include a virtual dental data set representing a different point in time than the virtual IDDS for a same patient. The different virtual dental data set may also include a virtual dental data set representing a different tooth configuration than that of the virtual IDDS for the same patient.

In such embodiments, the contexts of a particular view may result in easier landmark location identification as compared to a different view. For example, a reference point A selected from a particular perspective X of a configuration 1 may result in an increased ease in landmark location identification as compared to finding the same reference point A at the same perspective X at a different configuration 2.

FIGS. 2A-2F illustrate a number of example virtual IDDS and 3D dental elements of the virtual IDDS according to one or more embodiments of the present disclosure. With respect to FIG. 2A, during the manipulation of reference point 218 adhered to tooth 216 (e.g., tooth #10), tooth 214 (e.g., tooth #9) can be automatically made partially transparent or selected by a user to be made partially transparent because the visualization of the user-facing surface of tooth 216 can be beneficial as discussed above. Selecting reference point 218, for example, allows the user to move this reference point 218 along the surface of tooth 216, while using the outline of tooth 214 and its references (e.g., reference point 212 adjacent to reference point 218) to make decisions as to where to position the reference point 218, among other benefits.

Figure 2A:
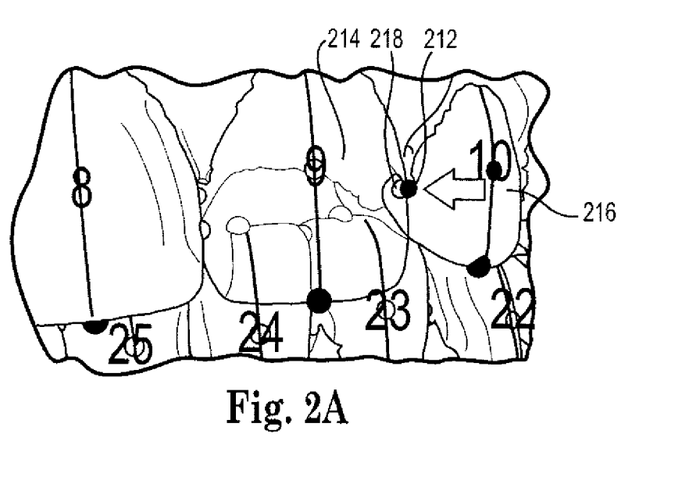
FIGS. 2A-2F illustrate example virtual initial dental data sets (IDDS) and 3D dental elements of virtual IDDS according to one or more embodiments of the present disclosure.

In some embodiments, the user can switch to the manipulation of references (e.g., reference point 212) which are adhered to tooth 214, but this may not change the transparency of tooth 214, because even though the reference is positioned on 214, the user may desire to see through the tooth 214 in order to properly position it relative to teeth 214 and 216 (and tooth 216's references). In some such embodiments, reference point 212 can only be moved around the surface of tooth 214, such that the reference point can be moved around the tooth surface, but cannot be removed from the tooth surface.

Figure 2B:
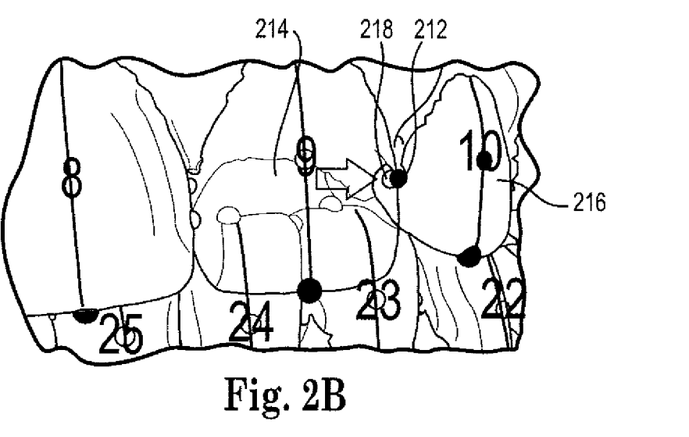

Therefore, depending on the orientation of the model relative to the user and the desired reference point to be selected, certain teeth and/or objects (e.g., gingiva, implants, references) in the scene can be made visually more transparent, as illustrated in FIG. 2B, so that the user can see behind the object, while preserving the ability to utilize the reference as a cue for orienting and/or positioning the reference(s). In the example illustrated in FIG. 2B, a first tooth 214 (e.g., tooth #9) is transparent, while a second tooth 216 (e.g., tooth #10) remains opaque.

Figure 2C:
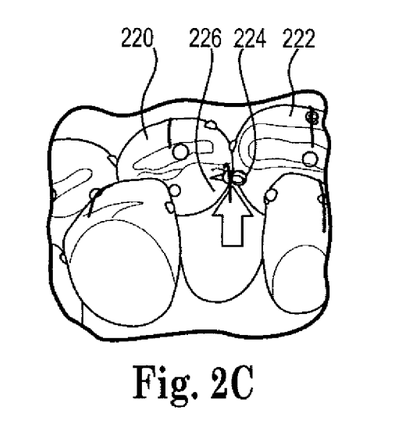

For example, as illustrated in FIG. 2C, a lower tooth 226 (e.g., tooth #26) may be hidden in order to adjust references pertaining to a view from underneath. For example, tooth 226 can be hidden (e.g., automatically hidden) to allow for adjustments of particular references. For example, the "incisal edge" reference 224 can be accessed and/or manipulated in light of upper teeth 220 and 222, without lower tooth 226's geometry getting in the way, which would be the case if it were not rendered in transparent mode.

Figure 2D:
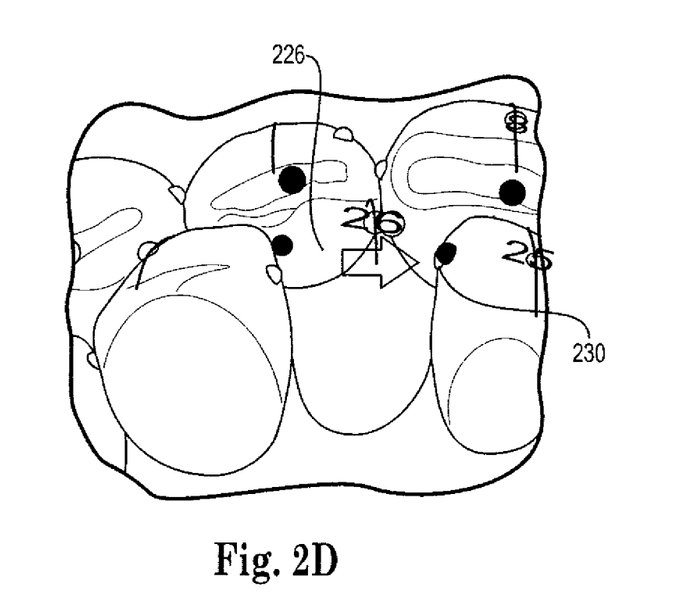

In an example, the incisal edge reference 224 on tooth 226 may not be seen or accessed because tooth 226 is in the way. As shown in FIG. 2D, however, an adjacent "interproximal" contact point 230 can also be manipulated as described previously for upper teeth 214 and 216 (e.g., teeth #9 and #10) with respect to FIG. 2A.

In such embodiments, computing device executable instructions can provide the ability to consider the line of sight of the user, (e.g., from the perspective of the user viewing via a user interface, such as a display) and the ability to render certain teeth more transparent allows the user to manipulate key dental references including points, lines, shapes, and the teeth themselves, without the hindrance of the object blocking the positioning of the desired reference. In such embodiments, the user can be able to effectively "see behind" the blocking object, while using the object's shape and/or position in the decision making process. Such embodiments may be useful when viewing the 3D space with a two dimensional or 3D user interface.

Furthermore, the user may be able to select the reference points and/or move them "through" the object in front of it. In other words, the blocking object can be ignored by the computing device executable instructions by giving the reference objects behind the object in front a higher priority in terms of selection.

In various embodiments, if a pointer is on a reference object, the reference object selection can be given a higher priority than the selection of the object which is visually (and in real life, physically) in front of the reference in the virtual space. In some such embodiments, this can allow the reference to be selected even though there may be another object in front of it.

Figure 2E:
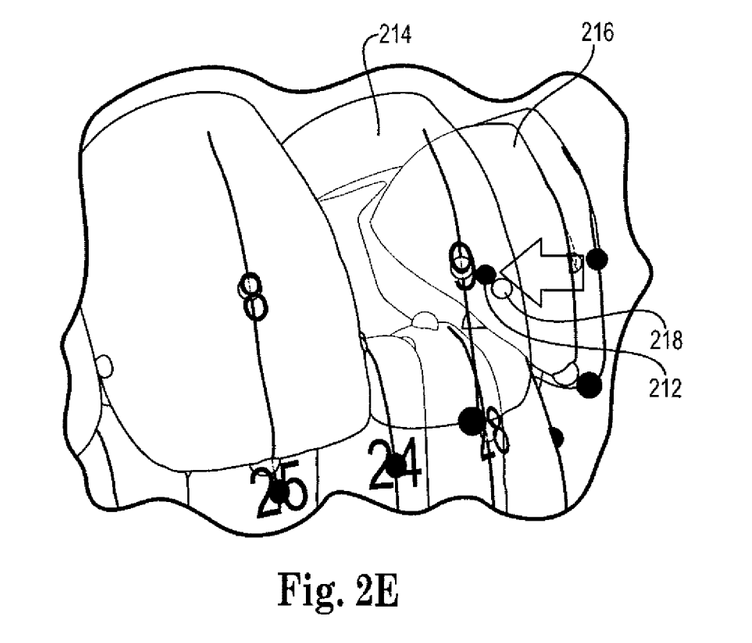

An example of the concept of prioritization is discussed with respect to FIG. 2E. For instance, tooth 214 (e.g., tooth #9), which is spatially "in front" of contact points 212 and 218, has one contact point that belongs to tooth 214 (e.g., tooth #9) and another to the adjacent tooth 216 (e.g., tooth #10).

From this view, both contact points 212 and 218 are sitting behind tooth 214. This view however, is the desired viewpoint because teeth naturally have an area where the contact points should be located. The problem is that tooth 214 is in the way of manipulation of the contact points.

In some embodiments, a "visual" prioritization could be to select the tooth 214 first when selecting an object in the area of the contact points 212 and 218 because tooth 214 is in front. However, by giving the contact point references a higher prioritization, tooth 214 is not selected when the user selects the pixels containing both tooth 214 and a contact point reference. Rather, the contact point references can be given a higher priority and therefore can be selected instead of the tooth. In some embodiments, this can result in an ability to adjust and/or view the contact point references even though tooth 214 is in front of the contact points 212 and 218.

Figure 2F:
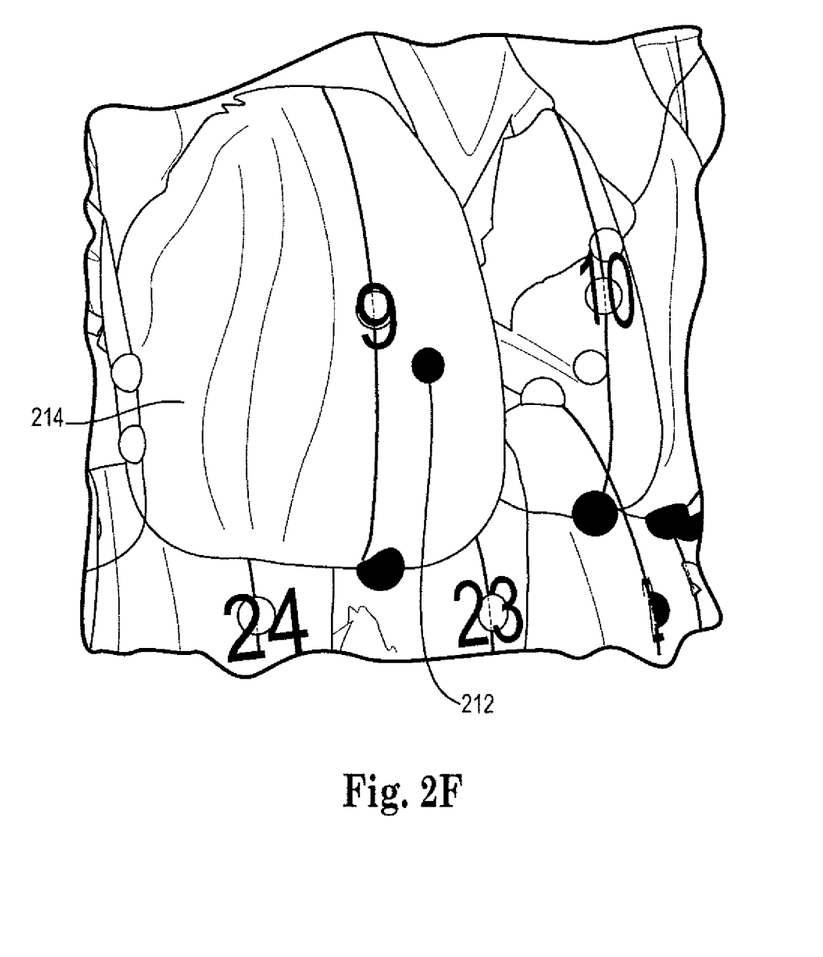

Another aspect of prioritization, in some embodiments, can be the positioning and/or placement of objects which are spatially behind other objects. In trying to move point 212, as illustrated in FIG. 2E, the typical behavior is for point 212 to be released after being selected on the front surface of tooth 214 (e.g., tooth #9) because this is the surface which is spatially in front, and normal selection behavior releases the object on the front-most object in spatial priority. The behavior taught in the present disclosure, however, is for point 212 to slide along the "back" or distal surface of tooth 214 and not brought to the front as shown in FIG. 2F.

In some typical concepts, the contact point behind the tooth is released on the front surface of the tooth. However, in the present disclosure, a contact point can be positioned on the "back" interproximal surface of the tooth even though the front surface is closer to the user in the user's view. In other words, the typical visual-spatial relationship (e.g., closest object to the viewer) can be ignored and a different prioritization for selection and placement of objects can be followed by the computing device executable instructions providing this functionality to the user.

Figure 3:
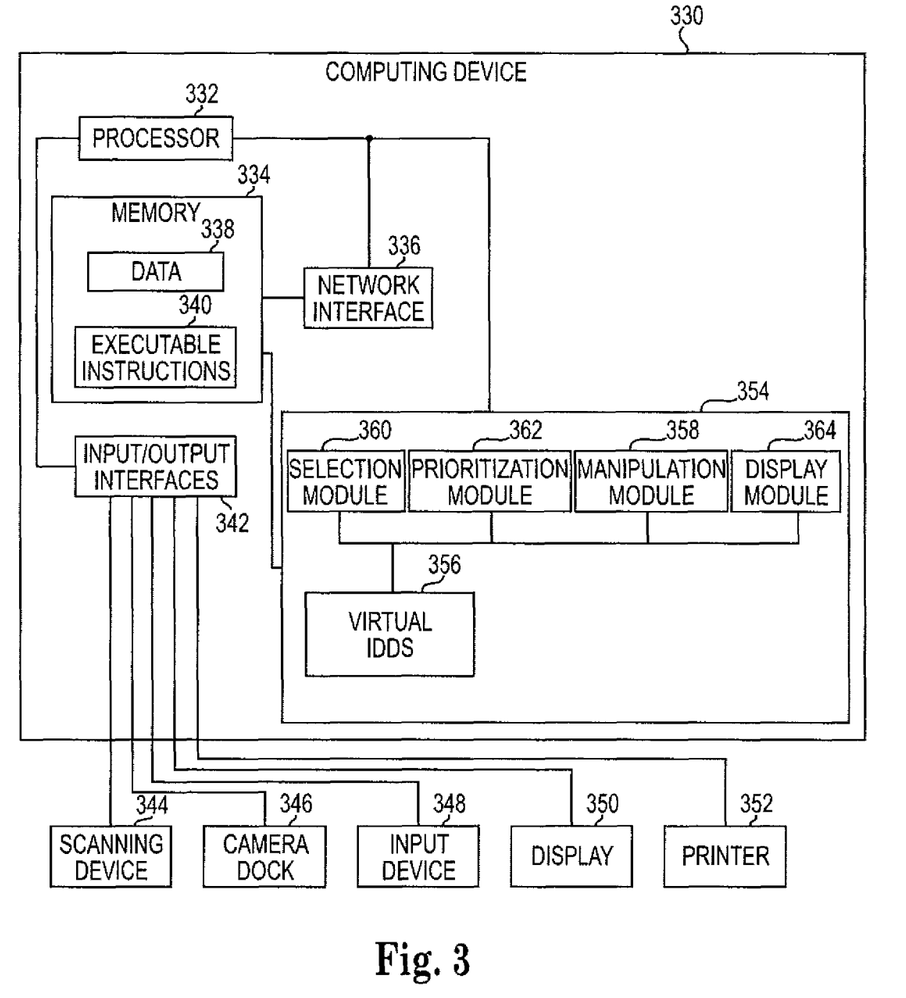
FIG. 3 illustrates a system for prioritizing 3D dental elements according to one or more embodiments of the present disclosure.

FIG. 3 illustrates a system for prioritizing 3D dental elements according to one or more embodiments of the present disclosure. In the system illustrated in FIG. 3, the system includes a computing device 330 having a number of components coupled thereto. The computing device 330 includes a processor 332 and memory 334. The memory can include various types of information including data 338 and executable instructions 340, as discussed herein.

Memory can be a non-transitory computing device readable medium that provides volatile or nonvolatile memory. The memory can also be removable (e.g., portable memory or non-removable, e.g., internal memory). For example, the memory can be random access memory (RAM) or read-only memory (ROM).

Memory can, for example, be dynamic random access memory (DRAM), electrically erasable programmable read-only memory (EEPROM), flash memory, phase change random access memory (PCRAM), compact-disk read-only memory (CD-ROM), a laser disk, a digital versatile disk (DVD) or other optical disk storage, and/or a magnetic medium such as magnetic cassettes, tapes, or disks, among other types of memory. Items stored in memory can include instructions executable by a computing device processor and/or data and the memory and processor can be located in one device or different devices.

Memory and/or the processor may be located on the computing device 330 or off the device, in some embodiments. As such, as illustrated in the embodiment of FIG. 3, a system can include a network interface 336. Such an interface can allow for processing on another networked computing device, can be used to obtain information about the patient, and/or can be used to obtain data and/or executable instructions for use with various embodiments provided herein.

As illustrated in the embodiment of FIG. 3, a system can include one or more input and/or output interfaces 342. Such interfaces can be used to connect the computing device with one or more input and/or output devices.

For example, in the embodiment illustrated in FIG. 3, the system can include connectivity to a scanning device 344, a camera dock 346, an input device 348 (e.g., a keyboard, mouse, etc.), a display device 350 (e.g., a monitor), a printer 352, and/or one or more other input devices. The input/output interface 342 can receive executable instructions and/or data, storable in the data storage device (e.g., memory 334), representing a digital dental model of a patient's dentition.

In some embodiments, the scanning device 344 can be configured to scan one or more physical molds of a patient's dentition. In one or more embodiments, the scanning device 344 can be configured to scan the patient's dentition directly. The scanning device 344 can be configured to input data into the computing device wherein the data can be provided to the application modules 354.

The camera dock 346 can receive an input from an imaging device (e.g., a two-dimensional or 3D imaging device) such as a digital camera, a printed photograph scanner, or other suitable imaging device. The input from the imaging device can, for example, be stored in the data storage device (e.g., memory 334).

The processor 332 can be configured to provide a visual indication of a virtual dental model on the display 350 (e.g., on a graphical user interface (GUI) running on the processor 332 and visible on the display 350). The GUI can be configured to allow a treatment professional or other user to input treatment goals, to create a virtual dental model, adjust priority levels, adjust references and other dental elements, and/or enter desired or actual attachment parameters. Input received via the GUI can be sent to the processor 332 as data and/or can be stored in memory 334.

Such connectivity can allow for the input and/or output of data and/or instructions among other types of information. Although some embodiments may be distributed among various computing devices within one or more networks, such systems as illustrated in FIG. 3, can be beneficial in allowing for the capture, calculation, and/or analysis of information discussed herein.

The processor 332, in association with the data storage device (e.g., memory 334), can be associated with data and/or application modules 354. The processor 332, in association with the memory 334, can store and/or utilize data and/or execute instructions to provide a number of application modules for prioritizing 3D dental elements. As used herein, a module can be a stand alone program, a portion of a program, or a set of code that provides a particular functionality.

Such data can include virtual IDDS 356. Such application modules can include a selection module 360, a prioritization module 362, a manipulation module 358, and/or a display module 364.

The selection module 360 can, for example, be configured to select a first element of a number of teeth in the virtual IDDS to be presented more transparently and a second element of the number of teeth in the virtual IDDS to be presented more opaquely.

The prioritization module 362 can be configured to prioritize the first and second elements based on the selection, and the manipulation module 358 can be configured to manipulate the first and second elements based on the prioritization, the transparency, and the opaqueness. In some embodiments, a user can determine a prioritization, and in other embodiments, the prioritization can be determined via computing device executable instructions. The display module 364 can be configured to display the manipulation on display device 350.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of appliances" can refer to one or more appliances.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A system for viewing three dimensional dental elements, comprising:
   a memory having computer-readable instructions stored thereon; and
   a processor coupled to the memory to execute the computer-readable instructions to:
      receive a virtual initial dental data set (IDDS) including spatial information regarding positions of a number of teeth in the virtual IDDS with respect to each other for presentation of the number of teeth in a virtual three dimensional space to be viewed on a user interface;
      determine a first transparency of a first tooth of the number of teeth based on an orientation of the virtual IDDS, wherein at least a portion of a second tooth of the number of teeth is behind the first tooth in the orientation of the virtual IDDS;
      receive, from a user, a selection of a reference point on the first tooth or the second tooth, wherein the reference point is located behind the first tooth in the orientation of the virtual IDDS; and
      manipulate the first transparency of the first tooth to a second transparency that is more transparent than the first transparency in response to selection of the reference point; and
      display, via the user interface, the first tooth having the second transparency so that the reference point is visible through the first tooth in the orientation of the virtual IDDS.

2. The system of claim 1, wherein the first tooth is more transparent than the second tooth.

3. The system of claim 1, wherein the processor coupled to the memory further executes the computer-readable instructions to prioritize the first tooth and the second tooth.

4. The system of claim 3, wherein the processor coupled to the memory further executes the computer-readable instructions to manipulate the first transparency of the first tooth and the second tooth based on prioritization of the first tooth and the second tooth.

5. The system of claim 1, wherein the processor coupled to the memory further executes the computer-readable instructions to manipulate the reference point from a first location on the first tooth to a second location on the first tooth.

6. The system of claim 1, wherein the dental elements include gingival surfaces, and wherein the number of teeth are prioritized over the gingival surfaces.

7. The system of claim 1, wherein the reference point corresponds to contact point of the first tooth and the second tooth.

8. The system of claim 1, wherein the computer-readable instructions further comprise instructions to receive user input to move the reference point along an edge of the second tooth behind the first tooth in the orientation of the virtual IDDS.

9. The system of claim 1, wherein the computer-readable instructions further comprise instructions to assigning the reference point a higher prioritization than the first tooth or the second tooth.

10. A non-transitory computing device readable medium having executable instructions that can be executed by a processor to:
- receive a virtual initial dental data set (IDDS) having spatial information regarding positions of a number of teeth in the virtual IDDS with respect to each other for presentation of the number of teeth in a virtual three dimensional space to be viewed on a user interface;
- determine a first transparency of a first tooth of the number of teeth relative to a second tooth of the number of teeth based on an orientation of the virtual IDDS, wherein at least a portion of the second tooth is behind the first tooth in the orientation of the virtual IDDS;
- receive, from a user, a selection of a reference point on the first tooth or the second tooth, wherein the reference point is located behind the first tooth in the orientation of the virtual IDDS; and
- manipulate the first transparency of the first tooth to a second transparency that is more transparent than the first transparency in response to selection of the reference point so that the reference point is visible through the first tooth in the orientation of the virtual IDDS.

11. The medium of claim 10, wherein the first transparency of the first tooth is made more transparent than the second tooth based on the first tooth being in front of the second tooth in the orientation of the virtual IDDS.

12. The medium of claim 10, wherein the instructions are executable by the processor to receive instructions from the user to move the reference point through the first tooth to a third tooth of the number of teeth.

13. The medium of claim 10, wherein the reference point is located on the second tooth, and wherein the instructions are executable by the processor to manipulate a location of the reference point on the second tooth while preventing the reference point from being moved off the second tooth.

14. A computing device implemented method of viewing three dimensional dental elements, comprising:
- receiving, by the computing device, a virtual initial dental data set (IDDS) having spatial information regarding positions of a number of teeth in the virtual IDDS with respect to each other;
- determining, by the computing device, a first transparency of a first tooth of the number of teeth based on an orientation of the virtual IDDS, wherein at least a portion of a second tooth of the number of teeth is behind the first tooth in the orientation of the virtual IDDS;
- receiving, by the computing device, a user selection of a reference point corresponding to a dental landmark of the first tooth and the second tooth, wherein the reference point is located behind the first tooth in the orientation of the virtual IDDS;
- manipulating, by the computing device, the first transparency of the first tooth to a second transparency that is more transparent than the first transparency based on the user selected reference point; and
- displaying, by the computing device, the first tooth having the second transparency so that the reference point is visible through the first tooth in the orientation of the virtual IDDS.

15. The method of claim 14, wherein the method includes transferring the dental landmark to a different virtual dental data set.

16. The method of claim 15, wherein the different virtual dental data set includes at least one of a first virtual dental data set representing a different point in time than the virtual IDDS for a same patient and a second virtual dental data set representing a different tooth configuration than that of the virtual IDDS for the same patient.

17. The method of claim 14, wherein the method includes selecting and manipulating the second tooth that is more opaque than the first tooth by a user via a user interface without selecting and manipulating the first tooth.

18. The method of claim 14, wherein the method includes labeling the dental landmark on the second tooth.

19. The method of claim 14, wherein the method includes prioritizing the first tooth and the second tooth.

20. The method of claim 19, wherein the method includes manipulating transparency of the first tooth and the second tooth based on prioritization of the first tooth and the second tooth.

* * * * *